United States Patent [19]
Ichihara

[11] Patent Number: 6,030,554
[45] Date of Patent: Feb. 29, 2000

[54] METHOD OF STERILIZING INTRAOCULAR LENS BY ELECTRON BEAM

[75] Inventor: Masuji Ichihara, Aichi-ken, Japan

[73] Assignee: Menicon Co., Ltd., Nagoya, Japan

[21] Appl. No.: 09/059,348

[22] Filed: Apr. 13, 1998

[30] Foreign Application Priority Data

Apr. 17, 1997 [JP] Japan .................................. 9-100302
Feb. 27, 1998 [JP] Japan .................................. 10-046685

[51] Int. Cl.⁷ ................................ G02F 1/00; F21V 9/04; A61L 2/00
[52] U.S. Cl. ............................ 252/583; 252/589; 422/22
[58] Field of Search ............................ 422/22; 252/582, 252/589, 583

[56] References Cited

U.S. PATENT DOCUMENTS

| | | | |
|---|---|---|---|
| 5,250,257 | 10/1993 | Lengfelder | 422/22 |
| 5,439,642 | 8/1995 | Hagmann | 422/22 |
| 5,617,154 | 4/1997 | Hoffman | 351/162 |

FOREIGN PATENT DOCUMENTS

| | | |
|---|---|---|
| 0 161 764 | 11/1985 | European Pat. Off. . |
| 0 308 130 | 3/1989 | European Pat. Off. . |
| 0 374 590 | 6/1990 | European Pat. Off. . |
| 0 544 926 | 6/1993 | European Pat. Off. . |
| 0 747 206 | 12/1996 | European Pat. Off. . |
| 196 23 289 | 12/1997 | Germany . |
| 6-90970 | 4/1994 | Japan . |
| 6-312013 | 11/1994 | Japan . |
| 2560164 | 12/1996 | Japan . |
| 942374 | 11/1963 | United Kingdom . |
| 92/00765 | 1/1992 | WIPO . |

*Primary Examiner*—Philip Tucker
*Attorney, Agent, or Firm*—Wall Marjama Bilinski & Burr

[57] ABSTRACT

A method of sterilizing an intraocular lens formed of a cross-linked polymer, wherein the intraocular lens is accommodated in a sealed container which permits transmission of an electron beam therethrough but inhibits entry of microorganisms thereinto, and the intraocular lens is irradiated with the electron beam, for sterilization of the intraocular lens accommodated in the container.

16 Claims, No Drawings

METHOD OF STERILIZING INTRAOCULAR LENS BY ELECTRON BEAM

The present application is based on Japanese Patent Application Nos. 9-100302 and 10-046685 filed Apr. 17, 1997, and Feb. 27, 1998, the content of which is incorporated hereinto by reference.

BACKGROUND OF THE INVENTION

1. Field of the Invention

The present invention relates to a method of sterilizing an intraocular lens, which method permits the intraocular lens to be sterilized in a short period of time in a simplified manner.

2. Discussion of the Related Art

Intraocular lenses have been used in cataract surgery. Namely, the intraocular lens is implanted in a human eye from which a crystalline lens has been removed in the cataract surgery. The intraocular lens includes an optical portion which serves as an optical lens to give a desired eyesight, and a support portion which holds the optical portion in position within the eye. As examples of such an intraocular lens, there are known a one-piece type intraocular lens in which the optical portion and the support portion are integrally formed of the same material, and a separate-piece type intraocular lens in which the optical portion and the support portion formed of respective different materials are assembled together. The optical and support portions of the intraocular lens are formed of a homopolymer or a copolymer of alkyl(meth)acrylate such as methyl methacrylate, or a silicone resin, for instance.

The intraocular lens which is implanted in the eye needs to be sterilized by a suitable sterilizing treatment after the intraocular lens is formed of a predetermined polymer. To this end, the intraocular lens is usually subjected to a sterilizing treatment using an ethylene oxide gas (hereinafter referred to as "EOG"), by taking account of the low heat-resistance of the intraocular lens. The sterilizing treatment using the EOG, however, causes various problems as described below.

By taking account of a possibility that the intraocular lens is contaminated with microorganisms after the sterilizing treatment, the intraocular lens is subjected to the sterilizing treatment while it is accommodated in a sterilizing bag formed of a suitable material which inhibits entry of the microorganisms. In other words, when the intraocular lens is sterilized by using the EOG, the intraocular lens must be accommodated in the sterilizing bag formed of a suitable gas-permeable material which permits transmission of the EOG therethrough. However, such a gas-permeable material is limited, and therefore the sterilizing bag formed of the material which permits the permeation of the EOG therethrough but inhibits the entry of the microorganisms thereinto undesirably tends to be very expensive.

Further, the use of the EOG gives rise to environmental pollution because of its toxicity. In addition, the intraocular lens which was sterilized by using the EOG must be subjected to aeration operation for a relatively long period of time for the purpose of removing the EOG, since the EOG which remains in the sterilizing bag is harmful.

Moreover, the sterilizing treatment using the EOG needs to be effected while accurately controlling the sterilizing conditions such as the temperature, humidity and concentration of the EOG, and inevitably requires an expensive sterilizing equipment. In addition, the EOG-sterilized intraocular lens must be subjected to a sterility test which lasts for at least 14 days. This is an obstacle to expeditious shipment or delivery of the product (intraocular lens), pushing up the cost of the intraocular lens.

Instead of using the EOG for sterilizing the intraocular lens, it is proposed to use gamma ($\gamma$) rays ("Eur. J. Implant Ref. Surg.", Vol. 1, March 1989, p.55–57). However, this method suffers from various problems. For instance, this method requires several hours, specifically, about 8 hours for completing the sterilization of the intraocular lens. Further, the material of the intraocular lens may be deteriorated due to reaction of the gamma irradiation and oxygen in the atmosphere or oxygen contained in the lens material. The degree of deterioration of the lens material will increase with an increase in the time period required for the sterilization treatment. In addition, it is troublesome to dispose of the radioactive material which was used for generating the gamma rays.

SUMMARY OF THE INVENTION

It is therefore an object of the present invention to provide an effective method of sterilizing an intraocular lens, in place of the conventional sterilizing method using the EOG or the gamma rays. It is an optional object of the present invention to provide a novel method of sterilizing an intraocular lens which does not require a special container with gas-permeability for accommodating the intraocular lens therein during the sterilizing treatment, and which method simplifies the process of the sterilization treatment of the intraocular lens.

The above objects may be attained according to the principle of the present invention, which provides a method of sterilizing an intraocular lens formed of a cross-linked polymer, comprising the steps of: accommodating the intraocular lens in a sealed container which permits transmission of an electron beam therethrough but inhibits entry of microorganisms thereinto; and irradiating the intraocular lens with the electron beam, for sterilization of the intraocular lens accommodated in the container.

According to the present method, since the intraocular lens is sterilized by irradiation with the electron beam, the intraocular lens can be sterilized in a considerably short period of time by utilizing the energy of the electron beam. Further, according to the present method, only the dose of the electron beam is required to be controlled during the sterilizing treatment, eliminating the cumbersome operation for controlling the various other sterilizing conditions as described above. Moreover, the present method eliminates the conventionally required sterility test, leading to simplification of the process of the sterilization treatment.

In the present invention, the intraocular lens to be sterilized is formed of a cross-linked polymer having three-dimensional cross-linked structure. The three-dimensional cross-linked structure is effective to inhibit or prevent reduction of the molecular weight of the cross-linked polymer immediately after its polymer chain is broken or cut by the irradiation of the electron beam. This arrangement effectively prevents deterioration of the mechanical strength and other properties of the intraocular lens, which would be caused by the electron beam irradiation. According to the present sterilizing method, even when the sterilized intraocular lens is brought into contact with, or dissolved in a solvent, the intraocular lens is not swollen with the solvent or dissolved in the solvent.

In one preferred form of the present invention, the intraocular lens is irradiated with the electron beam by a dose of 10–80 kGy, so that the intraocular lens can be effectively sterilized.

In another preferred form of the present invention, the cross-linked polymer of the intraocular lens contains an ultraviolet rays absorbent which is bonded thereto or mixed therewith. Owing to the inclusion of the ultraviolet rays (UV) absorbent in the cross-linked polymer of the intraocular lens, the UV transmittance property of the intraocular lens is made similar to that of natural crystalline lens, so as to reduce an adverse influence of the ultraviolet rays on the retina of the eye.

In general, the intraocular lens which contains the UV absorbent is apt to be colored by the electron beam radiation. In view of this, the intraocular lens which has been sterilized by the electron beam radiation is preferably subjected to an energy treatment selected from the group consisting of a thermal energy treatment, a light energy treatment, a radio-frequency energy treatment and a combination thereof, so that the intraocular lens is restored to its original color.

The thermal energy treatment for recovering the original color of the intraocular lens is preferably effected by heating the colored intraocular lens at a temperature which is 30° C. or higher and which is lower than the thermal deformation temperature of the intraocular lens, whereby the original color of the intraocular lens is effectively recovered.

DETAILED DESCRIPTION OF THE PREFERRED EMBODIMENT

The intraocular lens includes an optical portion and a support portion. Like the crystalline lens of the eye, the optical portion which serves as an optical lens gives a desired eyesight. The support portion holds the optical portion in position within the eye. The intraocular lens is classified into a one-piece type and a separate-piece type. In the one-piece type intraocular lens, the optical portion and the support portion are integrally formed of the same material. In the separate-piece type intraocular lens, the optical portion and the support portion formed of the respective different materials are assembled together.

The optical portion generally assumes a circular shape in front elevation. The optical portion may have a convex-convex configuration in side elevation in which the opposite surfaces are both convex, or a plano-convex configuration in which one of the opposite surfaces is convex and the other surface is planar. Alternatively, the optical portion may have a meniscus configuration in which one of the opposite surfaces is convex and the other surface is concave.

The support portion consists of thin rod members which extend outwardly from diametrically opposite positions of the periphery of the optical portion so as to provide curved support legs. Alternatively, the support portion may be of a so-called "boat-shaped" type consisting of an elliptical ring which supports the optical portion at a substantially central portion thereof.

In the present invention, each of the intraocular lenses having a desired shape as described above is formed of a predetermined cross-linked polymer. For instance, in the one-piece type intraocular lens, the entirety of the optical portion and the support portion is formed of a cross-linked polymer or copolymer obtained from a polymerization or copolymerization product of (meth)acrylate, i.e., acrylate or methacrylate. In the separate-piece type intraocular lens, the optical portion and/or the support portion are/is formed of the cross-linked polymer or copolymer as described above. More specifically described, the intraocular lens may have the optical portion formed of the cross-linked copolymer of the (meth)acrylate and the support portion formed of polypropylene or poly(vinylidene fluoride). Further, the intraocular lens may have the optical portion formed of a cross-linked polymer of polyolefin and the support portion formed of the cross-linked copolymer of the (meth)acrylate. The intraocular lens may have the optical portion formed of a soft cross-linked copolymer of (meth)acrylate and the support portion formed of a hard cross-linked copolymer of (meth)acrylate.

The cross-linked polymer of the intraocular lens according to the present invention has three-dimensional cross-linked structure which is introduced in the molecular structure or chain of the polymer. Any polymeric or polymerizable material used for forming a lens may be employed to provide the present cross-linked polymer, as long as the polymeric material is transparent and exhibits high stability. One example of such a polymeric material is an ethylenically unsaturated monomer such as: (meth)acrylates selected from the group consisting of methyl (meth)acrylate, ethyl (meth)acrylate, propyl (meth)acrylate, isopropyl (meth)acrylate, t-butyl (meth)acrylate, isobutyl (meth)acrylate, n-butyl (meth)acrylate, benzyl (meth)acrylate, cyclohexyl (meth)acrylate, 2-ethylhexyl (meth)acrylate, trifluoroethyl (meth)acrylate, hexafluoropropyl (meth)acrylate, and tetrafluoropropyl (meth)acrylate; and styrenes selected from the group consisting of styrene and α-methyl styrene. Only one of, or any combination of these ethylenically unsaturated monomers is mixed with a cross-linking agent formed of a polyfunctional monomer which will be described, so that the mixture is copolymerized and cross-linked so as to provide the cross-linked copolymer according to the present invention. Alternatively, the present cross-linked polymer is obtained by cross-linking a polyolefin polymer such as polypropylene in a known manner. In the present specification, the term ". . . (meth)acrylate" is generic to the following two compounds: ". . . acrylate" and ". . . methacrylate".

For enabling the intraocular lens to exhibit excellent optical properties, an acrylic cross-linked copolymer is advantageously used in the present invention which is obtained by copolymerization of one or more of the (meth)acrylates, especially, one or more of lower alkyl (C1–C4) esters of (meth)acrylate, and the cross-linking agent. Owing to the cross-linked structure introduced in the copolymer, even when the intraocular lens is brought into contact with or soaked in chemicals or solvents, the intraocular lens is effectively prevented from being swollen with or dissolved in the chemicals or solvents. In particular, when methyl methacrylate and/or ethyl methacrylate are/is used as the lower alkyl esters of (meth)acrylate, the obtained cross-linked copolymer which gives the intraocular lens is subjected to cutting and grinding operations with ease. Further, if the optical portion of the intraocular lens is formed of such a cross-linked copolymer, the intraocular lens has an effectively lowered photoelasticity coefficient, which means a small degree of optical distortion of the lens.

As the cross-linking agent which is copolymerized with the ethylenically unsaturated monomer as described above for introducing the three-dimensional cross-linked structure in the molecular structure of the polymer, a known polyfunctional monomer is suitably used which has two or more ethylenically unsaturated bonds and which is copolymerizable with the above-described unsaturated monomer of (meth)acrylate. Examples of such a polyfunctional monomer include ethylene glycol di(meth)acrylate, diethylene glycol di(meth)acrylate, trimethylolpropane tri(meth)acrylate, triethylene glycol di(meth)acrylate, allyl (meth)acrylate, 4-vinylbenzyl (meth)acrylate, and 3-vinylbenzyl (meth) acrylate. Only one of, or any combination of these polyfunctional monomers is used as the cross-linking agent. In the present invention, it is particularly preferable to use ethylene glycol di(meth)acrylate. Since the ethylene glycol di(meth)acrylate can be easily purified, it is obtained with a high yield, so as to efficiently provide the cross-linked copolymer by copolymerization with the (meth)acrylate. The use of the ethylene glycol di(meth)acrylate is particularly preferable when the lower alkylester of (meth)acrylate is used as the polymeric material since the ethylene glycol di(meth)acrylate is easily copolymerizable with the lower alkylester of (meth)acrylate.

If the cross-linking agent is used in an excessive amount, the cross-linked copolymer obtained by copolymerization of the ethylenically unsaturated monomer and the cross-linking agent tends to be brittle because the cross-linked copolymer is excessively cross-linked. On the contrary, if the amount of the cross-linking agent is insufficient, the degree of cross-linking of the obtained cross-linked copolymer is considerably low, whereby the lens material, accordingly, the intraocular lens itself does not enjoy the advantages to be exhibited by the cross-linked structure. In view of this, it is preferable that the cross-linked copolymer be formed by copolymerization of 70–99.99 wt. % of at least one ethylenically unsaturated monomer as described above, and 0.01–30 wt. % of the cross-linking agent. For attaining an adequate degree of cross-linking, the cross-linked copolymer is preferably formed by copolymerization of 80–99.9 wt. % of at least one ethylenically unsaturated monomer and 0.1–20 wt. % of the cross-linking agent.

The cross-linked polymer which provides the intraocular lens may contain additives such as an ultraviolet rays (UV) absorbent and a coloring agent, as needed, which are conventionally used for intraocular lenses. The UV absorbent and the coloring agent may be mixed with the cross-linked polymer, or may be chemically bonded with molecules in the cross-linked polymer by copolymerization. The UV absorbent and the coloring agent to be contained in the cross-linked polymer are suitably selected so that the UV absorbent and the coloring agent are not adversely influenced by chemicals or pharmaceuticals used for ophthalmological purposes, and so that the selected UV absorbent and the coloring agent are not easily removed from the cross-linked polymer. In view of this, it is preferable to use a polymeric or polymerizable UV absorbent such as benzophenone, benzotriazole, and derivatives of salicylic acid, which have a polymeric group such as an acryloyl group, a methacryloyl group, a vinyl group, an allyl group, or an isopropenyl group. As the coloring agent, it is preferable to use a polymeric or polymerizable coloring agent such as azo, anthraquinone, nitro, or phthalocyanine having the polymeric groups as described above. These UV absorbent and the coloring agent are copolymerized together with the unsaturated monomer and the cross-linking agent. The UV absorbent and the coloring agent are mixed with the cross-linked polymer or chemically bonded to the cross-linked polymer by polymerization, so that the retina of the eye is effectively protected from the influence of the ultraviolet rays and so that a difference in the color vision (color sense) of the intraocular lens with respect to the normal eye is minimized.

The cross-linked polymer as described above is formed into the intraocular lens having a desired configuration, according to any known methods. For instance, the intraocular lens is produced by cutting and grinding a mass or blank of the cross-linked polymer. The intraocular lens may be produced by molding in which a monomer mixture which gives the cross-linked polymer is poured into a mold having a cavity which corresponds to the contour of the intraocular lens to be obtained, and then the monomer mixture in the mold is polymerized so as to provide the intraocular lens having the desired configuration. Further, the intraocular lens may be produced according to a so-called "semi-molding" method in which one of the opposite surfaces of the intraocular lens is formed by molding and the other surface is formed by cutting and grinding operations. The intraocular lens may also be produced by casting such as spin casting or static casting.

The principle of the present invention is applicable to various types of intraocular lenses having the optical portion and the support portion of known configurations. The configuration and the number of the support portions are not particularly limited. The support portion may have free ends, or may take the form of a loop connected to the periphery of the optical portion. The principle of the present invention is applicable to the intraocular lenses having various optical portions with different optic properties, such as a mono-focal optic portion, a bi-focal optical portion, and a multiple-focal optical portion. Further, the principle of the present invention is applicable to a toric intraocular lens whose optic portion has a dioptric power which varies continuously in the circumferential direction of the optic portion. The surfaces of the optic portion may be formed in any shape, such as convex, flat or concave.

According to the present invention, the intraocular lens formed of the cross-linked polymer as described above is irradiated with the electron beam for effecting a sterilization treatment thereon. In the sterilization treatment, the intraocular lens is irradiated with the electron beam while it is accommodated in a suitable gas-tightly sealed container, so as to prevent contamination of the intraocular lens.

The container for accommodating the intraocular lens during the electron beam radiation may be formed of any high-molecular material such as polyethylene, polypropylene, polystyrene, polyester, polyamide or polycarbonate, provided that the material permits transmission of the electron beam through the container but inhibits entry of the microorganisms into the container. Alternatively, the container may be formed of a glass material, a ceramic material, or a metallic material since such materials permit transmission of the electron beam therethrough if they are used in relatively small thickness. As the container, any known gas-tightly sealed bag or box may be used as long as it accommodates at least one intraocular lens. Further, the intraocular lens may be accommodated in a suitable gas-tightly sealed container as described above with the lens being kept in a conventionally used lens case.

According to the present invention, the conventionally used bag-like or box-type sealed container made of vinyl, for instance, can be used as the container for accommodating the intraocular lens. Therefore, the present arrangement does not require a special gas-permeable container which has been conventionally used in the sterilization treatment using the EOG, leading to a considerably reduced cost of manufacture of the container.

The intraocular lens accommodated in a suitable container as described above is irradiated with the electron beam, so that the intraocular lens can be sterilized. The electron beam which irradiates the intraocular lens is easily transmitted through the container so as to reach the intraocular lens accommodated therein, whereby the intraocular lens can be sterilized as needed. The present sterilization treatment using the electron beam is free from various problems such as environmental pollution and gas leakage which were conventionally experienced in the sterilization treatment using the EOG. Further, the sterilization treatment can be effected by controlling only the dose of the electron beam, so that the sterilization treatment is facilitated. The present arrangement eliminates the aeration operation conventionally effected after the sterilization treatment for minimizing the EOG which remains in the lens material, whereby the sterilization process is simplified.

Owing to the irradiation of the intraocular lens with the electron beam, the amount of the unpolymerized monomer which remains in the cross-linked polymer of the intraocular lens, in particular, in the acrylic cross-linked copolymer which is mainly formed of (meth)acrylate, is decreased. For instance, the percentage of the unpolymerized monomer in the cross-linked polymer is reduced from about 0.8% to about 0.2% after the electron beam irradiation. This feature is advantageous since the intraocular lens implanted in the eye semipermanently functions in place of the natural crystalline.

The electron beam (corpuscular beam) which irradiates the intraocular lens is accelerated by an electron beam accelerator so as to increase its energy. The electron beam accelerator for producing the electron beam having a high kinetic energy is classified into an electrostatic type and a linear type, and is widely used in the scientific, industrial and medical fields, for example. The intraocular lens is sterilized by using such a known electron beam accelerator.

The electron beam which irradiates the intraocular lens is accelerated at a voltage of generally not lower than 500 KV, preferably at a voltage of not lower than 1000 KV. If the accelerating voltage of the electron beam is lower than 500 KV, the transmission capacity of the electron beam is lower than 1000 g/m$^2$ (which is equivalent to the transmission distance of 1 mm at a density of 1 g/cm$^3$), so that the electron beam does not reach the thickness center of the intraocular lens whose thickness may be as large as 1.5 mm. In this case, the intraocular lens can not be sufficiently sterilized. When the intraocular lens is accommodated in a predetermined container with the lens being kept in a suitable box or lens case, the electron beam is preferably accelerated at a voltage of not lower than 1000 KV at which the electron beam has the transmission capacity of above 3000 g/m$^2$. The accelerating voltage of the electron beam is suitably determined such that the transmission distance of the electron beam is long enough to sterilize the intraocular lens and the container.

The intraocular lens is irradiated with the electron beam for sterilization for a time period of generally not more than ten minutes, preferably not more than five minutes, more preferably not more than one minute. Since the intraocular lens can be sterilized by the electron beam irradiation for a considerably short period of time, the required delivery time of the intraocular lens can be reduced, and the material of the intraocular lens is not damaged by the electron beam irradiation. In particular, the intraocular lens is formed of the cross-linked polymer according to the present invention, so that the deterioration of the material of the intraocular lens by the electron beam irradiation can be effectively minimized. Thus, the physical properties of the the intraocular lens are not deteriorated by the sterilization treatment.

In the present sterilizing method, the intraocular lens is irradiated with the electron beam by a dose of 10–80 kGy, preferably 15–70 kGy. If the intraocular lens is irradiated with the electron beam by a dose of lower than 10 kGy, the intraocular lens is not sufficiently sterilized. On the other hand, if the intraocular lens is irradiated with the electron beam by a dose of above 70 kGy, the material of the lens tends to be deteriorated, and the intraocular lens is colored to an excessive extent.

In the present sterilization treatment by the electron beam irradiation, only the dose of the electron beam which irradiates the intraocular lens is required to be measured and controlled, eliminating the accurate control of various other sterilizing conditions such as the concentration, temperature, humidity, time and pressure, as required in the conventional sterilization treatment using the EOG. Since the present arrangement does not require the sterility test conventionally effected after the intraocular lens is sterilized by the EOG, the required delivery time of the product (intraocular lens) can be significantly reduced. In addition, the intraocular lens can be produced at a reduced cost.

The material for providing the intraocular lens may contain additives, as needed, such as the UV absorbent as described above, so as to give the desired properties to the intraocular lens. When the intraocular lens which contains the additives such the UV absorbent is irradiated with the electron beam, the intraocular lens tends to be colored. For instance, the UV absorbent is easily excited, i.e., colored, by the energy of the electron beam. More specifically described, the intraocular lens which contains the benzotriazole UV absorbent turns yellow while the intraocular lens which contains the benzophenone UV absorbent turns pink.

The color of the intraocular lens which was caused due to the excitation of the UV absorbent is removed with a lapse of time. However, after the electron beam irradiation, the intraocular lens is preferably subjected to a color restoring or recovering treatment using an energy for recovering the original color of the lens, which energy is selected from the group consisting of a thermal energy, a light energy, a radio-frequency energy, and a combination thereof. This energy treatment can quickly recover the original color of the intraocular lens.

When the thermal energy is used for the color recovering treatment, the intraocular lens (especially, its support portion which has a smaller thickness than the optic portion) is heated to a temperature which is 30° C. or higher and which is lower than a thermal deformation temperature of the intraocular lens. The intraocular lens accommodated in the predetermined container is preferably heated to a temperature which is lower by about 10° C. than the thermal deformation temperature of the intraocular lens. The thermal deformation temperature is generally a temperature at which the intraocular lens undergoes thermal deformation. More specifically described, the thermal deformation temperature causes changes in the optical properties of the intraocular lens. For instance, the refracting power of the intraocular lens is changed by not less than 0.5 diopter, and the resolving power is changed by not less than 10% when the intraocular lens is kept at the thermal deformation temperature for 8 hours. Alternatively, the Sagitta of the intraocular lens is changed by not less than 0.05 mm at the thermal deformation temperature.

If the intraocular lens is heated to an excessively high temperature, the intraocular lens, especially its support portion tends to be deformed. On the other hand, if the lens is heated to an excessively low temperature, it requires a relatively long period of time to restore the original color of the lens, or the color of the lens is not removed to a satisfactory degree. In view of this, the intraocular lens is heated to a temperature which is 30° C. or higher, preferably 40° C. or higher, more preferably 50° C. or higher. Further, the time period during which the intraocular lens is heat-treated preferably ranges from 4 hours to 2 weeks, since the heat treatment for an excessively long time period is not economical, and the heat treatment for an excessively short time period does not provide an intended effect.

The intraocular lens may be subjected to the color recovering treatment using an energy other than the thermal energy as described above, such as a light energy which utilizes natural or artificial light, or a radio-frequency energy which utilizes a micro wave. Further, the intraocular lens may be subjected to the color recovering treatment using the thermal energy, light energy and radio-frequency energy in combination. The frequency and the intensity of the light and the radio-frequency wave, and the time period of the energy treatment are suitably determined so as to obtain a desired effect. When the intraocular lens is subjected to the color recovering treatment which utilizes the thermal energy, light energy and radio-frequency energy in combination, the conditions of the energy treatment are suitably determined while taking account of the characteristics of each energy.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

Example 1

Initially, there was prepared a monomer composition by mixing 97 wt. % of methyl methacrylate (as one example of alkyl methacrylate) and 3 wt. % of ethylene glycol dimethacrylate as a cross-linking agent. To this monomer composition, 0.005 wt. % of 2,2'-azobis(2,4-dimethyl valeronitrile) as a polymerization initiator was added, so as to provide a polymeric mixture. The thus obtained polymeric mixture was put into a test tube having a diameter of 18 mm. After the test tube was sealed, it was heated at different temperatures for respective periods, namely, at 35° C. for five days, at 40° C. for one day, at 45° C. for one day, at 50–90° C. for one day, and at 100–130° C. for one day, in the order of description. Thus, a cross-linked copolymer was obtained by copolymerization and cross-linking of methyl methacrylate and ethylene glycol dimethacrylate.

The thus obtained cross-linked copolymer was taken out of the test tube, and put into a drier. After the cross-linked copolymer was kept in the drier at 130° C. for eight hours, it was gradually cooled for the purpose of removing distortion of the cross-linked copolymer. Thereafter, the cross-linked copolymer was subjected to a cutting operation using a lathe, to thereby provide a cylindrical member having a thickness of 3 mm and a diameter of 15.5 mm. The obtained cylindrical member was subjected to conventional cutting and grinding operations, so as to provide a plurality of one-piece type intraocular lenses each having an optical portion with a 6.0 mm-diameter and a 0.80 mm-thickness at its central portion. The optical portion of each lens has a dioptric power of +20 D as converted refractive power in eye.

The plurality of intraocular lenses prepared as described above were respectively put into conventionally used lens cases formed of a styrene-butadiene copolymer material. Each intraocular lens kept in the lens case was then accommodated in a sealed bag formed of polyethylene, and was irradiated with an electron beam by a dose of 25 kGy which was accelerated at a voltage of 5000 KV by using an electron beam irradiation apparatus "Dinamitron" (5 Mev) manufactured by Radiation Dynamics Inc., USA. Thus, the plurality of intraocular lenses were sterilized.

Among the plurality of intraocular lenses sterilized as described above, randomly selected three lenses were subjected to a sterility test as specified in the Japanese Pharmacopoeia (12th revision). It was confirmed that all of the three lenses were free of microorganisms. Each lens was taken out of the sealed bag and was visually observed. It was confirmed that all of the three lenses remained colorless and transparent even after the sterilization treatment. Each of the sterilized lenses was crushed, and immersed in tetrahydrofuran for one week. Like the intraocular lens before the sterilization treatment, the crushed lens was not dissolved in tetrahydrofuran, making it impossible to measure its molecular weight. This fact indicates that the cross-linked structure of the cross-linked copolymer of the intraocular lens was maintained after the sterilization treatment, and that the cross-linked copolymer kept a high molecular weight.

Comparative example 1

100 wt. % of methyl methacrylate was polymerized in the same manner as in the above Example 1, so as to provide a non cross-linked polymer (polymethyl methacrylate). That is, the cross-linking agent (ethylene glycol dimethacrylate) was not used in this Comparative example 1. The thus obtained non cross-linked polymer was subjected to the distortion removing operation, and formed into a cylindrical member, in the same manner as in the above Example 1. Thereafter, the cylindrical member was subjected to the cutting and grinding operations, so that the a plurality of intraocular lenses were obtained. The thus obtained lenses were irradiated with the electron beam for sterilization, as in the Example 1.

The intraocular lenses sterilized as described above were subjected to the sterility test as in the Example 1. It was confirmed that all of the lenses were free of microorganisms. Further, the sterilized intraocular lenses were visually inspected. The result of the visual inspection showed that the intraocular lenses remained colorless and transparent even after the sterilization treatment.

The sterilized intraocular lenses were immersed in the tetrahydrofuran. Like the intraocular lenses before the sterilization treatment, the sterilized intraocular lenses in this comparative example were dissolved in the tetrahydrofuran. The solution of the tetrahydrofuran in which the intraocular lenses were dissolved was measured of its molecular weight by gel permeation chromatography. According to the measurement, the number average molecular weight of the intraocular lens was reduced from 2,000,000 to 200,000 after the sterilization treatment by the electron beam irradiation. This fact indicates that the molecular weight of the non cross-linked polymer (polymethyl methacrylate) of the intraocular lens was considerably reduced because its polymer chain was cut or broken by the electron beam irradiation.

Example 2

To the monomer composition prepared in the Example 1, there was added, as a UV absorbent, 0.18 wt. % of 2-[2'-hydroxy-5'-(2"-methacryloyloxyethoxy)-3'-tertiary-butylphenyl]-5-methyl-2H-benzotriazole. This mixture was polymerized in the same manner as in the Example 1, so that a desired cross-linked copolymer was obtained.

As in the Example 1, the thus obtained cross-linked copolymer was subjected to the distortion removing operation, and was formed into a cylindrical member. Then, the cylindrical member was subjected to the cutting and grinding operations as in the Example 1, so as to provide a plurality of intraocular lenses. The obtained intraocular lenses were irradiated with the electron beam for sterilization, in the same manner as in the Example 1.

The sterilized intraocular lenses were subjected to the sterility test as in the Example 1. It was confirmed that all of the lenses were free of microorganisms. The sterilized intraocular lenses were visually inspected, and it was confirmed that the lenses turned yellow. Like the intraocular lenses before the sterilization treatment, the sterilized intraocular lenses were not dissolved in the tetrahydrofuran after the immersion therein.

Some of the sterilized intraocular lenses which had turned yellow by the electron beam irradiation were kept at the room temperature for one month. The yellow color of the intraocular lenses did not fade after the one-month storage at the room temperature. The other of the sterilized intraocular lenses which had turned yellow were kept at 50° C. for 10 days. It was confirmed that the yellow color of the intraocular lenses faded, and that these intraocular lenses became colorless.

Example 3

A desired cross-linked copolymer was obtained by polymerization in the same manner as in the above Example 1, except that methyl methacrylate was replaced with ethyl methacrylate. The obtained cross-linked copolymer was subjected to the distortion removing operation, and was formed into a cylindrical member. Then, the cylindrical member was subjected to the cutting and grinding operations, so that a plurality of intraocular lenses were obtained.

The thus obtained intraocular lenses were irradiated with the electron beam for sterilization, in the same manner as in the Example 1.

The intraocular lenses sterilized as described above were subjected to the sterility test as in the Example 1. It was confirmed that all of the lenses were free of microorganisms. Further, the sterilized intraocular lenses were visually inspected. The result of the visual inspection showed that the sterilized intraocular lenses remained colorless and transparent even after the sterilization treatment. Like the intraocular lenses before the sterilization treatment, the sterilized intraocular lenses were not dissolved in the tetrahydrofuran after the immersion therein.

Example 4

To the monomer composition prepared in the above Example 1, there were added a UV absorbent, namely, 0.18 wt. % of 2-[2'-hydroxy-5'-(2"-methacryloyloxyethoxy)-3'-tertiary-butylphenyl]-5-methyl-2H-benzotriazole, and coloring agents, namely, 0.0016 wt. % of 1-phenylazo-3-methacryloyloxy-2-naphthalenol and 0.015 wt. % of a sodium salt of 1-(4-chlor-2-sulfophenyl)-3-methyl-4-[para-(paratolyl-sulfonoxy)-phenylazo]-5-pyrazolone. The thus prepared mixture was polymerized as in the Example 1, so that an intended colored cross-linked copolymer was obtained.

The thus obtained colored cross-linked copolymer was subjected to the distortion removing operation, and was formed into a cylindrical member. Then, the obtained cylindrical member was subjected to the cutting and grinding operations, so that a plurality of intraocular lenses were obtained.

The thus prepared intraocular lenses were irradiated with the electron beam for sterilization, as in the Example 1.

The sterilized intraocular lenses were subjected to the sterility test in the same manner as in the Example 1. It was confirmed that the all of the lenses were free of microorganisms. Further, the sterilized intraocular lenses were visually inspected. The result of the visual inspection showed that the sterilized lenses were deeply colored. Like the intraocular lenses before the sterilization treatment, the sterilized intraocular lenses were not dissolved in the tetrahydrofuran after the immersion therein.

Some of the sterilized lenses were kept at the room temperature for one month. The color of these lenses did not fade after the one-month storage at the room temperature. The other of the sterilized lenses were kept at 50° C. for 10 days. It was confirmed that the deep color of these lenses disappeared, and that the original color of the lenses were recovered.

It will be understood from the above description that the method of sterilizing the intraocular lens according to the present invention permits the intraocular lens to be sterilized in a considerably reduced time period, unlike the conventional sterilizing method using the EOG, and eliminates the conventionally effected aeration operation and sterility test. The present arrangement simplifies the sterilization process, so that the intraocular lens can be sterilized in a comparatively short time period, and therefore, the delivery time of the intraocular lens can be effectively shortened.

According to the present sterilizing method, the conventionally used sealed bag made of vinyl, for example, can be used as the container for accommodating the intraocular lens, without using a specific container having gas-permeability. Further, the present sterilizing method is free from the conventionally experienced problems of the residual toxic gas and the environmental pollution. In addition, the intraocular lens can be sterilized according to the present invention by controlling only the dose of the electron beam which irradiates the intraocular lens, so that the sterilization treatment is simplified.

What is claimed is:

1. A method of sterilizing an intraocular lens formed of a cross-linked polymer, comprising the steps of:

accommodating said intraocular lens in a sealed container which permits transmission of an electron beam therethrough but inhibits entry of microorganisms thereinto; and irradiating said intraocular lens with said electron beam, for sterilization of said intraocular lens accommodated in said container.

2. A method according to claim 1, wherein said cross-linked polymer of said intraocular lens is obtained by copolymerization of at least one of acrylate and methacrylate, and a cross-linking agent formed of a polyfunctional monomer.

3. A method according to claim 2, wherein said polyfunctional monomer is ethylene glycol diacrylate.

4. A method according to claim 2, wherein said polyfunctional monomer is ethylene glycol dimethacrylate.

5. A method according to claim 1, wherein said intraocular lens is irradiated with said electron beam by a dose of 10–80 kGy.

6. A method according to claim 1, wherein said intraocular lens is irradiated with said electron beam for a time period of not more than ten minutes.

7. A method according to claim 1, wherein said electron beam is accelerated at a voltage of not lower than 500 KV.

8. A method according to claim 1, wherein said electron beam is accelerated at a voltage of not lower than 1000 KV.

9. A method according to claim 1, wherein said cross-linked polymer contains said at least one of acrylate and methacrylate in an amount of 70–99.99 wt. % and said cross-linking agent in an amount of 0.01–30 wt. %.

10. A method according to claim 1, wherein said cross-linked polymer contains said at least one of acrylate and methacrylate in an amount of 80–99.9 wt. % and said cross-linking agent in an amount of 0.1–20 wt. %.

11. A method according to claim 1, wherein said cross-linked polymer further contains an ultraviolet rays absorbent which is bonded thereto or mixed therewith.

12. A method according to claim 1, wherein said cross-linked polymer further contains a coloring agent.

13. A method according to claim 1, further comprising the step of effecting an energy treatment of said intraocular lens selected from the group consisting of a thermal energy treatment, a light energy treatment, a radio-frequency energy treatment and a combination thereof.

14. A method according to claim 13, wherein said thermal energy treatment is effected by heating said intraocular lens at a temperature which is 30° C. or higher and which is lower than a thermal deformation temperature of said intraocular lens.

15. A method according to claim 13, wherein said thermal energy treatment is effected by heating said intraocular lens at a temperature which is 40° C. or higher and which is lower than a thermal deformation temperature of said intraocular lens.

16. A method of sterilizing an intraocular lens formed of a cross-linked polymer, comprising the steps of:

accommodating said intraocular lens in a sealed container which permits transmission of an electron beam therethrough but inhibits entry of microorganisms thereinto; and irradiating said intraocular lens with said electron beam by a dose of 10–80 kGy for a time period of not more than ten minutes, for sterilization of said intraocular lens accommodated in said container, said electron beam being accelerated at a voltage of not lower than 500 KV.

* * * * *